United States Patent
Vandommele et al.

(10) Patent No.: US 10,891,503 B2
(45) Date of Patent: Jan. 12, 2021

(54) METHOD AND DEVICE FOR CLASSIFYING EYE OPENING DATA OF AT LEAST ONE EYE OF AN OCCUPANT OF A VEHICLE, AND METHOD AND DEVICE FOR DETECTING DROWSINESS AND/OR MICROSLEEP OF AN OCCUPANT OF A VEHICLE

(71) Applicant: Robert Bosch GmbH, Stuttgart (DE)

(72) Inventors: Tjark Vandommele, Stuttgart (DE); Felix Wulf, Ludwigsburg (DE)

(73) Assignee: Robert Bosch GmbH, Stuttgart (DE)

(*) Notice: Subject to any disclaimer, the term of this patent is extended or adjusted under 35 U.S.C. 154(b) by 328 days.

(21) Appl. No.: 16/061,642

(22) PCT Filed: Nov. 10, 2016

(86) PCT No.: PCT/EP2016/077248
§ 371 (c)(1),
(2) Date: Jun. 12, 2018

(87) PCT Pub. No.: WO2017/102186
PCT Pub. Date: Jun. 22, 2017

(65) Prior Publication Data
US 2020/0265251 A1    Aug. 20, 2020

(30) Foreign Application Priority Data
Dec. 14, 2015   (DE) .................. 10 2015 225 109

(51) Int. Cl.
*G06K 9/00* (2006.01)
*G06K 9/62* (2006.01)
*G06T 7/20* (2017.01)

(52) U.S. Cl.
CPC ..... *G06K 9/00845* (2013.01); *G06K 9/00604* (2013.01); *G06K 9/6218* (2013.01);
(Continued)

(58) Field of Classification Search
CPC .......... G06K 9/00845; G06K 9/00604; G06K 9/6218; G06K 9/6267; G06T 7/20; G06T 2207/30196
See application file for complete search history.

(56) References Cited

U.S. PATENT DOCUMENTS

| | | | | |
|---|---|---|---|---|
| 5,805,720 A | * | 9/1998 | Suenaga ............ | G06K 9/00597 340/575 |
| 6,097,295 A | | 8/2000 | Griesinger et al. | |

(Continued)

FOREIGN PATENT DOCUMENTS

| | | |
|---|---|---|
| CN | 101132729 A | 2/2008 |
| CN | 101583313 A | 11/2009 |

(Continued)

OTHER PUBLICATIONS

Effects of Driver fatigue—Survey, Katja Karrer et al., Springer, 2007, pp. 324-330 (Year: 2007).*

(Continued)

*Primary Examiner* — Jayesh A Patel
(74) *Attorney, Agent, or Firm* — Norton Rose Fulbright US LLP; Gerard Messina

(57) ABSTRACT

A method for classifying eye opening data of an occupant's eye in a vehicle, to detect drowsiness/microsleep, including generating a first eye opening data record at a first measuring time in a sliding time window, the first record including a measuring point, representing a first eye opening degree, a first eyelid speed and/or acceleration of motion of the occupant's eye at the first measuring time; acquiring a second eye opening data record at a second measuring time, the second record including at least one acquisition point, representing a second eye opening degree, a second eyelid speed of motion and/or acceleration of motion of the occupant's eye; and executing a cluster analysis, using the measuring point and the acquisition point to assign at least (Continued)

the first and/or second record to a first data cluster, to classify the eye opening data; the first cluster representing an opening state of the occupant's eye.

12 Claims, 7 Drawing Sheets

(52) U.S. Cl.
CPC .............. *G06K 9/6267* (2013.01); *G06T 7/20* (2013.01); *G06T 2207/30196* (2013.01)

(56) References Cited

U.S. PATENT DOCUMENTS

| | | | |
|---|---|---|---|
| 6,975,902 B2 * | 12/2005 | Phipps | A61N 1/0448 604/20 |
| 7,362,885 B2 * | 4/2008 | Hammoud | G06K 9/00604 382/100 |
| 2005/0213792 A1 * | 9/2005 | Hammoud | G06T 7/248 382/103 |
| 2005/0232461 A1 * | 10/2005 | Hammoud | G06K 9/00604 382/103 |
| 2006/0204042 A1 * | 9/2006 | Hammoud | G06K 9/00832 382/107 |
| 2008/0037837 A1 | 2/2008 | Noguchi et al. | |
| 2008/0101659 A1 * | 5/2008 | Hammoud | G06K 9/00597 382/118 |
| 2008/0218359 A1 | 9/2008 | Ishida et al. | |
| 2008/0238694 A1 * | 10/2008 | Ishida | B60K 28/066 340/575 |
| 2009/0244274 A1 | 10/2009 | Morita et al. | |
| 2009/0268022 A1 * | 10/2009 | Omi | A61B 5/18 348/135 |
| 2010/0036290 A1 * | 2/2010 | Noguchi | A61B 5/165 600/595 |
| 2011/0216181 A1 * | 9/2011 | Yoda | A61B 5/1103 348/78 |
| 2011/0313259 A1 * | 12/2011 | Hatakeyama | B60K 28/06 600/300 |
| 2014/0147019 A1 * | 5/2014 | Hanita | G06T 7/90 382/117 |
| 2014/0152792 A1 * | 6/2014 | Krueger | G06K 9/00604 348/78 |
| 2016/0140390 A1 * | 5/2016 | Ghosh | G06K 9/00617 348/78 |
| 2016/0314366 A1 * | 10/2016 | Omi | H04N 5/23229 |

FOREIGN PATENT DOCUMENTS

| | | | | |
|---|---|---|---|---|
| DE | 19715519 A1 | | 11/1997 | |
| EP | 2453427 A1 | | 5/2012 | |
| JP | H07313459 A | | 12/1995 | |
| JP | 2006209582 A | * | 8/2006 | |
| JP | 2008099884 A | | 5/2008 | |
| JP | 5262819 B2 | | 8/2013 | |
| JP | 2013257691 A | | 12/2013 | |
| WO | 2006092022 A1 | | 9/2006 | |
| WO | WO-2006092022 A1 | * | 9/2006 | ............... A61B 5/18 |
| WO | 2007145566 A1 | | 12/2007 | |
| WO | 2014031042 A1 | | 2/2014 | |

OTHER PUBLICATIONS

International Search Report for PCT/EP2016/077248, dated Jan. 25, 2017.
The Lid Closing Behavior as an Indicator of Attention and Fatigue Processes During Work Actions 2002. http://www.psychologie.uni-wuerzburg.de/izvw/texte/2003_hargutt_Das_Lidschlussverhalten.pdf.

* cited by examiner

METHOD AND DEVICE FOR CLASSIFYING EYE OPENING DATA OF AT LEAST ONE EYE OF AN OCCUPANT OF A VEHICLE, AND METHOD AND DEVICE FOR DETECTING DROWSINESS AND/OR MICROSLEEP OF AN OCCUPANT OF A VEHICLE

FIELD OF THE INVENTION

The present invention is directed to a device or a method according to the definition of the species in the independent claims. The subject matter of the present invention also includes a computer program.

BACKGROUND INFORMATION

Drowsiness and microsleep at the wheel frequently result in dangerous situations or accidents. Today's drowsiness detection systems output a warning, when the driver exceeds a certain limiting drowsiness value. A symbol, such as a coffee cup, is then made visible in the field of view of the driver to indicate the exceedance of the limiting drowsiness value.

For example, drowsiness detection systems currently in production estimate the fatigue of the driver indirectly from the driving behavior. In addition, systems are known, which are able to detect the current degree of opening of the eyes. This is accomplished, using suitable image processing algorithms. In this context, a level of eye opening is detected, in each instance, for the two eyes.

Patent document WO 2014/031042 A1 discusses a system, which fits an eye opening signal to predefined, modeled signals, in order to detect blinking events and to draw conclusions from them, regarding the attentiveness of the driver.

Patent document WO 2006/092022 discusses a system, which uses a so-called reference amplitude for "normal" blinking events in order to detect blinking events from the eye opening signal.

Correlations between the characteristics of blinking events and drowsiness have already been discussed in the literature, cf. Hargutt: Das Lidschlussverhalten als Indikator für Aufmerksamkeits- and Müdigkeitsprozesse bei Arbeitshandlungen [The Lid Closing Behavior as an Indicator of Attention and Fatigue Processes during Work Actions], 2002.

SUMMARY OF THE INVENTION

Against this background, a method for classifying eye opening data of at least one eye of an occupant of a vehicle, a method for detecting drowsiness and/or microsleep of an occupant of a vehicle, furthermore, a device that applies these methods, and finally, a corresponding computer program, according to the main description, are introduced, using the starting point put forward here. Advantageous further refinements and improvements of the device indicated herein are rendered possible by the measures specified and described herein.

Acquisition of eye opening data and/or of an eye opening signal in a sliding time window, and subsequent execution of a cluster analysis of these data, allows the quality of detection of blinking characteristics of the eyes of a vehicle occupant to be improved.

In one further refinement, the concept proposed here includes an improved method for calculating a current eye opening level or eye opening niveau (EON).

A method for classifying eye opening data of at least one eye of an occupant of a vehicle, in order to detect drowsiness and/or microsleep of the occupant is put forward, the method including the following steps:

generating a first eye opening data record at a first measuring time in a sliding time window, the first eye opening data record including at least one measuring point, which represents a first eye opening degree and/or a first eyelid speed of motion and/or a first eyelid acceleration of motion of the eye of the occupant at the first measuring time;

acquiring a second eye opening data record at a second measuring time in the sliding time window, the second eye opening data record including at least one acquisition point, which represents a second eye opening degree and/or a second eyelid speed of motion and/or a second eyelid acceleration of motion of the eye of the occupant at the second measuring time; and executing a cluster analysis, using the at least one measuring point and the at least one acquisition point, to assign at least the first eye opening data record and/or second eye opening data record to a first data cluster, in order to classify the eye opening data, the first data cluster representing an opening state of the eye of the occupant.

The eye opening data may include data of an eye opening degree of the eye, as well as data of a speed and/or an acceleration of a movement of the eyelids of the eye at one time. The eye opening degree may be a distance from the upper to the lower eyelid of the eye of the occupant at the first and/or second measuring time, the distance being determined in meters or centimeters or millimeters. The eye opening data may be provided in the form of a signal over a plurality of measuring times. Classifying the eye-opening data may be understood to mean assigning the eye-opening data to predetermined categories of states of the eye. For example, states of the eye may be distinguished as open, closed, or in an opening or closing phase. The first and/or second eye-opening data record may represent an ascertained or acquired value of a state of the eye of the occupant, the value also being able to be depicted in a coordinate system. The first eye-opening data record may include a suitable combination of data of the first eye-opening degree, the first eyelid speed of motion and the first eyelid acceleration of motion of the eye of the occupant. The same may apply analogously to the second eye opening data record. The measuring point may constitute a value on a coordinate axis for depicting a first eye opening data record. Accordingly, the acquisition point may constitute a value on a coordinate axis for depicting a second eye opening data record. The second measuring time may lie temporally after the first measuring time in a sliding time window. The cluster analysis is to be understood as a method for discovering patterns of similarity in stored data of the eye opening data records. The cluster analysis may be, for example, a density-based cluster analysis. In this case, existing patterns of similarity of the data may be represented by a cluster formation of the data in the coordinate system, that is, by a grouping of the data in the coordinate space to form data clusters. Using the opening state of the eye, it may be stated how far the eye of the occupant is open or closed.

This method may be implemented, for example, as software or hardware, or in a combined form of software and hardware, in, for example, a control unit or a device.

According to one specific embodiment, in the generating step, the first eye opening data record may include at least one further measuring point, which represents a first eye opening degree not represented by the measuring point and/or a first eyelid speed of motion and/or a first eyelid acceleration of motion of the eye of the occupant at the first measuring time. Alternatively, or in addition, in the acquisition step, the second eye opening data record may include at least one further acquisition point, which represents a second eye opening degree not represented by the acquisition point and/or a second eyelid speed of motion and/or a second eyelid acceleration of motion of the eye of the occupant at the second measuring time. Accordingly, in the execution step, the cluster analysis may also be executed, using the further measuring point and/or the further acquisition point. The further measuring point and/or the further acquisition point may advantageously contribute to a robust detection of eye movement features of the occupant. In this connection, the further measuring point represents another parameter from the set of parameters of eye opening degree, first eyelid speed of motion and/or first eyelid acceleration of motion of the eye of the occupant as the measuring point, which means that the measuring points of the first eye opening data record are based on measuring points, which represent different physical quantities. In an analogous manner, the further acquisition point represents another parameter from the set of parameters of eye opening degree, eyelid speed of motion and/or eyelid acceleration of motion of the eye of the occupant as the acquisition point, which means that the acquisition points of the second eye opening data record are based on acquisition points, which represent different physical quantities.

The method may further include a step of averaging, using the measuring point and the acquisition point, if the first eye opening data record and the second eye opening data record are assigned to the first data cluster. In this manner, a first parameter of the first data cluster may be calculated, the first parameter being able to represent a value for an eye opening niveau of the eye of the occupant, if the measuring point and the acquisition point represent eye opening degrees of the eye. In this connection, the measuring point and the acquisition point should represent the same physical quantities. The eye opening niveau is to be understood as an average eye opening degree within the sliding time window. The eye opening niveau may be measured in meters. According to this specific embodiment, the eye opening niveau, which is essential for detecting drowsiness or microsleep of the occupant, may be ascertained rapidly and robustly.

According to one specific embodiment, in the averaging step, the measuring point and the acquisition point may be averaged in a weighted manner, in order to determine the first parameter. Thus, the eye opening niveau may be determined even more reliably.

For example, in the averaging step, the measuring point may be weighted as a function of the acquisition point, in order to determine the first parameter. In particular, the measuring point may be weighted as a function of a value of the acquisition point, in order to determine the first parameter. In this connection, the measuring point may be weighted as a function of a value of the acquisition point, in particular, as a function of a difference of a value of the measured value and the value of the acquisition point. In this context, in particular, a magnitude of this difference may be used for weighting the measuring point and/or the acquisition point. Using such a density-dependent weighting, measuring errors and inaccuracies may advantageously be prevented from invalidating a result of the eye opening niveau to be ascertained.

According to one specific embodiment, the method may include a step of discarding the second eye opening data record, if the second eye opening data record is not assigned to the first data cluster. Thus, in the method, computing expenditure may easily be reduced, in particular, if the second eye opening data record is possibly unusable due to measuring errors.

According to a further specific embodiment, in the execution step, the first eye opening data record is assigned to the first data cluster, and the second eye opening data record is assigned to a second data cluster, in order to classify the eye opening data; the second data cluster representing a further opening state of the eye of the occupant. The assignment of the eye opening data records to different data clusters allows eye movement characteristics, such as occupant blinking movements and glances at the speedometer, to be detected simply and robustly.

For example, in the execution step, the opening state represents an open eye of the occupant, and the further opening state represents a closed eye of the occupant.

According to a further specific embodiment, the method includes a step of inputting a third eye opening data record at a third measuring time in the sliding time window. The third eye opening data record may include at least one determination point, which represents a third eye opening degree and/or a third eyelid speed of motion and/or a third eyelid acceleration of motion of the eye of the occupant at the third measuring time. Accordingly, in the execution step, the cluster analysis may be executed, using the at least one determination point of the third eye opening data record, to assign the third eye opening data record to a third data cluster, in order to classify the eye opening data. The third data cluster may represent a transition state of the eye of the occupant. The determination point may constitute a value on a coordinate axis for depicting a third eye opening data record. According to this specific embodiment, the discrimination between different eye movement characteristics may be improved even further.

The transition state of the eye of the occupant may represent an opening phase or a closing phase of the eye.

A method for detecting drowsiness and/or microsleep of an occupant of the vehicle is also put forward, the method (800) including the following step:

ascertaining drowsiness and/or microsleep, using eye opening data classified according to a method, as shown in one of the specific embodiments specified above.

The approach put forward here further provides a device, which is configured to perform, control and/or implement the steps of a variant of a method put forward here, in corresponding devices.

The object of the present invention may also be achieved rapidly and efficiently by this embodiment variant of the present invention, in the form of a device.

To this end, the device may include at least one arithmetic unit for processing signals or data, at least one storage unit for storing signals or data, at least one interface to a sensor or to an actuator for inputting sensor signals from the sensor or for outputting data signals or control signals to the actuator, and/or at least one communications interface for inputting or outputting data, which are embedded in a communications protocol. The arithmetic unit may be, for example, a signal processor, a microcontroller or the like, the storage unit being able to be a flash memory, an EPROM or a magnetic storage unit. The communications interface may be configured to input or output data wirelessly and/or in a line-conducted manner; a communications interface, which can input or output line-conducted data, being able to input or output these data, for example, electrically or optically, from a corresponding data transmission line or to a corresponding data transmission line.

In the case at hand, a device may be understood as an electrical device that processes sensor signals and outputs control and/or data signals as a function of them. The device may have an interface, which may be implemented as hardware and/or software. In a hardware configuration, the interfaces may, for example, be part of a so-called system ASIC that includes many different functions of the device. However, it is also possible for the interfaces to be separate, integrated circuits or to be at least partially made up of discrete components. In a software configuration, the interfaces may be software modules that are present, for example, on a microcontroller in addition to other software modules.

In one advantageous refinement, the device uses a density-based cluster analysis to filter out eye movement characteristics or eye characteristics of at least one eye of the occupant from the eye opening signal, in order to detect drowsiness or to detect microsleep.

Also advantageous is a computer program product or computer program, including program code, which may be stored on a machine-readable carrier or storage medium, such as a solid state memory, a hard disk storage device or an optical storage device, and is used for performing, implementing and/or controlling the steps of a method according to one of the above-described specific embodiments, in particular, when the program product or program is executed on a computer or a device.

Exemplary embodiments of the present invention are represented in the drawing and explained in greater detail in the following description.

DETAILED DESCRIPTION

Figure 1:
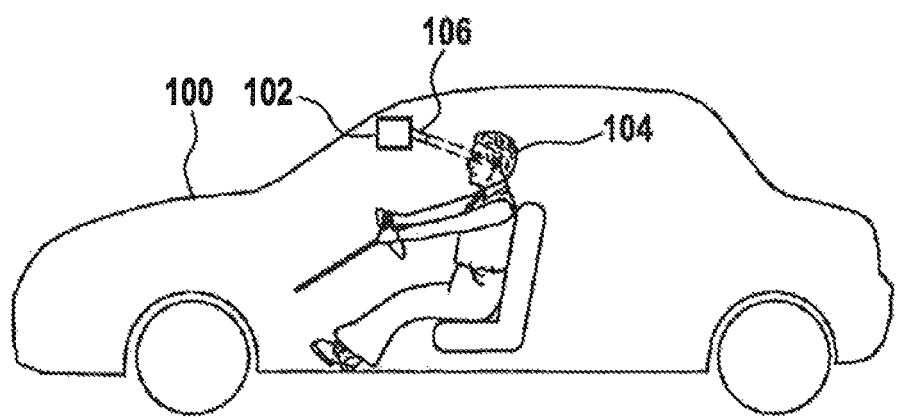
FIG. 1 shows a schematic representation of a vehicle having a device for detecting drowsiness and/or microsleep of an occupant of the vehicle, according to an exemplary embodiment.

In the following description of the exemplary embodiments of the present invention, the same or similar reference numerals are used for the elements that are shown in the different figures and function similarly, in which case a repeated description of these elements is omitted.

FIG. 1 shows a schematic representation of a vehicle 100 having a device 102 for detecting drowsiness and/or microsleep of an occupant 104 of vehicle 102, according to an exemplary embodiment. Vehicle 100 is a passenger car. Alternatively, vehicle 100 may also be a different on-road vehicle, such as a cargo truck. In this case, occupant 104 is a driver 104 of vehicle 100.

In this connection, device 102 is connected to a camera 106, which is installed in vehicle 100 and monitors the eyes of driver 104. In particular, camera 106 records a position of the eyelids of the eyes of driver 104, for example, a distance between the eyelids of at least one of the eyes, and a speed and/or an acceleration of a movement of the eyelids of at least one of the eyes. This information may be combined to form eye opening data, which, according to the approach put forward here, are classified and processed in device 102, in order to detect a drowsiness state or microsleep of driver 104 of vehicle 100.

Figure 2:
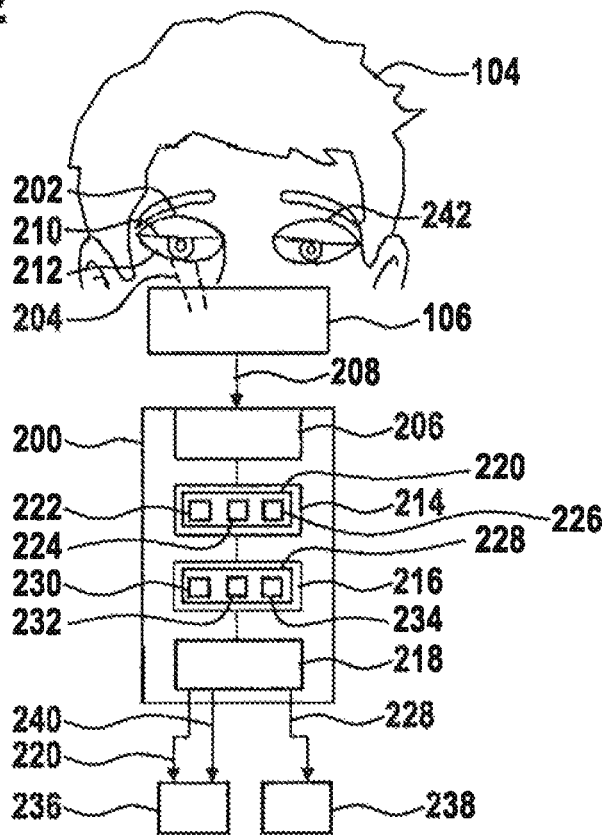
FIG. 2 shows a block diagram of a device for classifying eye opening data of an occupant of a vehicle, according to an exemplary embodiment.

FIG. 2 shows a block diagram of a device 200 for classifying eye opening data of an occupant 104 of a vehicle, according to an exemplary embodiment. Eye opening data classified with the aid of device 200 may be used in the device shown in FIG. 1 for detecting drowsiness and/or microsleep. Device 200 is part of the device for detecting drowsiness and/or microsleep shown in FIG. 1, or is, or may be, coupled to it. Device 200 is configured to classify eye opening data of at least one eye 202 of occupant 104, in this case, right eye 202.

The camera 106 pointed towards the eyes of occupant 104 receives an eye opening signal 204 of right eye 202 of occupant 104. Eye opening signal 204 includes measurements of movements of the eyelids of eye 202 over a plurality of measuring times. Consequently, eye opening signal 204 represents a characteristic of the eye opening data over a plurality of times.

An input device 206 of device 200 inputs the eye opening data 208 forming eye opening signal 204 into device 200, via a suitable interface. Eye opening data 208 include information regarding an eye opening degree, a speed, as well as an acceleration of the eyelids of eye 202 at a measuring time, during the monitoring of eye 202. Eye opening data 208, i.e., eye opening signal 204, are acquired by camera 106 or a device coupled to camera 106, in a sliding time window.

The eye opening degree is to be understood as a distance from an upper eyelid 210 to a lower eyelid 212 of eye 202 at a measuring time. The eye opening degree is measured in meters. The speed and the acceleration of eyelids 210, 212 are measured in complete or incomplete opening and/or closing phases of eyelids 210, 212.

In addition to input device 206, device 200 includes a generating device 214, an acquisition device 216 and an execution device 218.

Generating device 214 is configured to generate a first eye opening data record 220 at a first measuring time in the sliding time window, based on eye opening data 208. According to one exemplary embodiment, first eye opening data record 220 includes a measuring point 222, a further measuring point 224 and a second further measuring point 226. For example, measuring point 222 represents a first eye opening degree of eye 202 at the first measuring time, further measuring point 224 represents an eyelid speed of motion of at least one of the eyelids 210, 212 of occupant 104 at the first measuring time, and second further measuring point 226 represents an eyelid acceleration of motion of eye 202 of occupant 104 at the first measuring time.

Acquisition device 216 is configured to acquire a second eye opening data record 228 at a second measuring time in the sliding time window, based on eye opening data 208. According to an exemplary embodiment, second eye opening data record 228 includes an acquisition point 230, a further acquisition point 232, and a second further acquisition point 234. For example, acquisition point 230 represents a second eye opening degree of eye 202 at the second measuring time, further acquisition point 232 represents an eyelid speed of motion of at least one of eyelids 210, 212 of occupant 104 at the second measuring time, and second further acquisition point 234 represents an eyelid acceleration of motion of eye 202 of occupant 104 at the second measuring time.

In accordance with exemplary embodiments, there may be more or less than the three measuring points 222, 224, 226 and respective acquisition points 230, 232, 234 for forming eye opening data records 220, 228. Depending on the exemplary embodiment of device 200, eye opening data records 220, 228 may be constituted of different combinations of the eye opening degree, eyelid speed of motion and eyelid acceleration of motion of eye 202. In addition, only subsets of these data may be included in eye opening data records 220, 228.

Execution device 218 is configured to execute a cluster analysis of eye opening data records 220, 228, using measuring points 222, 224, 226 and acquisition points 230, 232, 234, by applying suitable algorithms. In accordance with a result of the cluster analysis, execution device 218 assigns first eye opening data record 220 to a first data cluster 236 from a plurality of data clusters, and assigns second eye opening data record 228 to a second data cluster 238 from the plurality of data clusters. According to one exemplary embodiment, the two eye opening data records 220, 228 may also be assigned, e.g., to first data cluster 236. This is the case, for example, if first measuring time 222 and second measuring time 224 are temporally very close together and/or first acquisition point 230 and second acquisition point 232 are temporally very close together.

According to an alternative exemplary embodiment, execution device 218 may be configured to discard second eye opening data record 228, if second eye opening data record 228 is not assigned to first data cluster 236.

Eye opening data records 220, 228 are classified by assigning eye opening data records 220, 228 to data clusters 236, 238, that is, to one of a plurality of opening states or transition states of the eye 202 monitored by camera 106. For example, first data cluster 236 defines a possible, first opening state of eye 202, in which eye 202 is open, and second data cluster 238 defines a possible, second opening state of eye 202, in which eye 202 is closed. According to exemplary embodiments, a third data cluster may define a possible, first transition state of eye 202, in which eye 202 is in an opening phase, and a fourth data cluster may define a possible, second transition state of eye 202, in which eye 202 is in a closing phase.

Of course, device 200 may also be configured to process more than the two data records 220, 228, using its devices 206, 214, 216, 218, and to assign them to one or more data clusters 236, 238.

According to one exemplary embodiment of the concept introduced here, for the case in which first eye opening data record is 220 and second eye opening data record 228 are assigned to first data cluster 236, and for the case in which measuring point 222 and acquisition point 230 each represent an eye opening degree, execution device 218 or another device of device 200 is configured to subject eye opening data records 220, 228 to an averaging operation, using at least one of measuring points 222, 224, 226 and acquisition points 230, 232, 234. In this manner, a parameter 240, which represents a highly robust value for an eye opening niveau of eye 222 of occupant 104, is formed for first data cluster 236.

The eye opening niveau, abbreviated as EON, is a value for the average eye opening degree within a time window; times, at which the eye is not completely open, such as squints or blinking events or glances at the speedometer, being disregarded. The eye opening niveau is measured in meters and is essential for as error-free as possible a detection of drowsiness or microsleep by the device shown in FIG. 1.

According to one exemplary embodiment, the averaging operation, which is carried out in device 200 and is for determining the parameter 240 for first data cluster 236, may be a weighted averaging operation.

For all of the data clusters 236, 238 present, parameters assigned to them may be calculated in device 200 in a manner analogous to the procedure described above.

For the exemplary case, in which execution device 218 executes a density-based cluster analysis, then, in the weighted averaging operation, measuring point 222 and/or further measuring points 224, 226 are weighted as a function of acquisition point 230 and/or further acquisition points 232, 234. It is particularly advantageous, when measuring point(s) 222, 224, 226 are weighted as a function of a proximity to acquisition point(s) 230, 232, 234, in order to determine parameter 240.

Of course, in a manner analogous to the procedure explained above, device 200 may additionally or alternatively classify eye opening data of left eye 242 of occupant 104 simultaneously to, or temporally offset with respect to, the calculations for right eye 202, in order to prepare or support a drowsiness or microsleep analysis of occupant 104.

Figure 3:
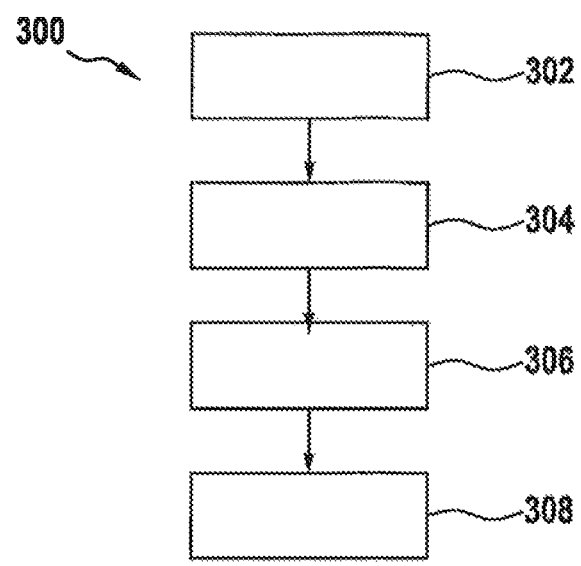
FIG. 3 shows a flow chart of a method for classifying eye opening data of an occupant of a vehicle, according to an exemplary embodiment.

FIG. 3 shows an exemplary embodiment of a flow chart of a method 300 for classifying eye opening data of an occupant of a vehicle. Method 300 may be executed by the device for classifying shown in FIG. 2, and/or by its devices.

In a generating step 302, a first eye opening data record including at least one measuring point is generated at a first measuring time in a sliding time window. In an acquisition step 304, a second eye opening data record including at least one acquisition point is acquired at a second measuring time in the sliding time window. In an execution step 306, a cluster analysis is executed, using the measuring point and the acquisition point, to assign the first eye opening data record and/or second eye opening data record to a first data cluster, in order to classify the eye opening data.

According to one exemplary embodiment, method 300 includes a step 308 of averaging the first eye opening data record and the second eye opening data record, using the measuring point and the acquisition point, in order to calculate a first parameter of the first data cluster.

FIGS. 4 through 7 show graphs for representing data clusters of eye opening data, generated according to the computational method from FIG. 3, according to one exemplary embodiment. In each instance, a coordinate system is shown, in which a plurality of data clusters ascertained according to the computational method are depicted schematically as a cloud. In the FIGS. 4 through 7, which show the graphs from different viewing angles, all of the graphs are based on a single computation.

Figure 4:
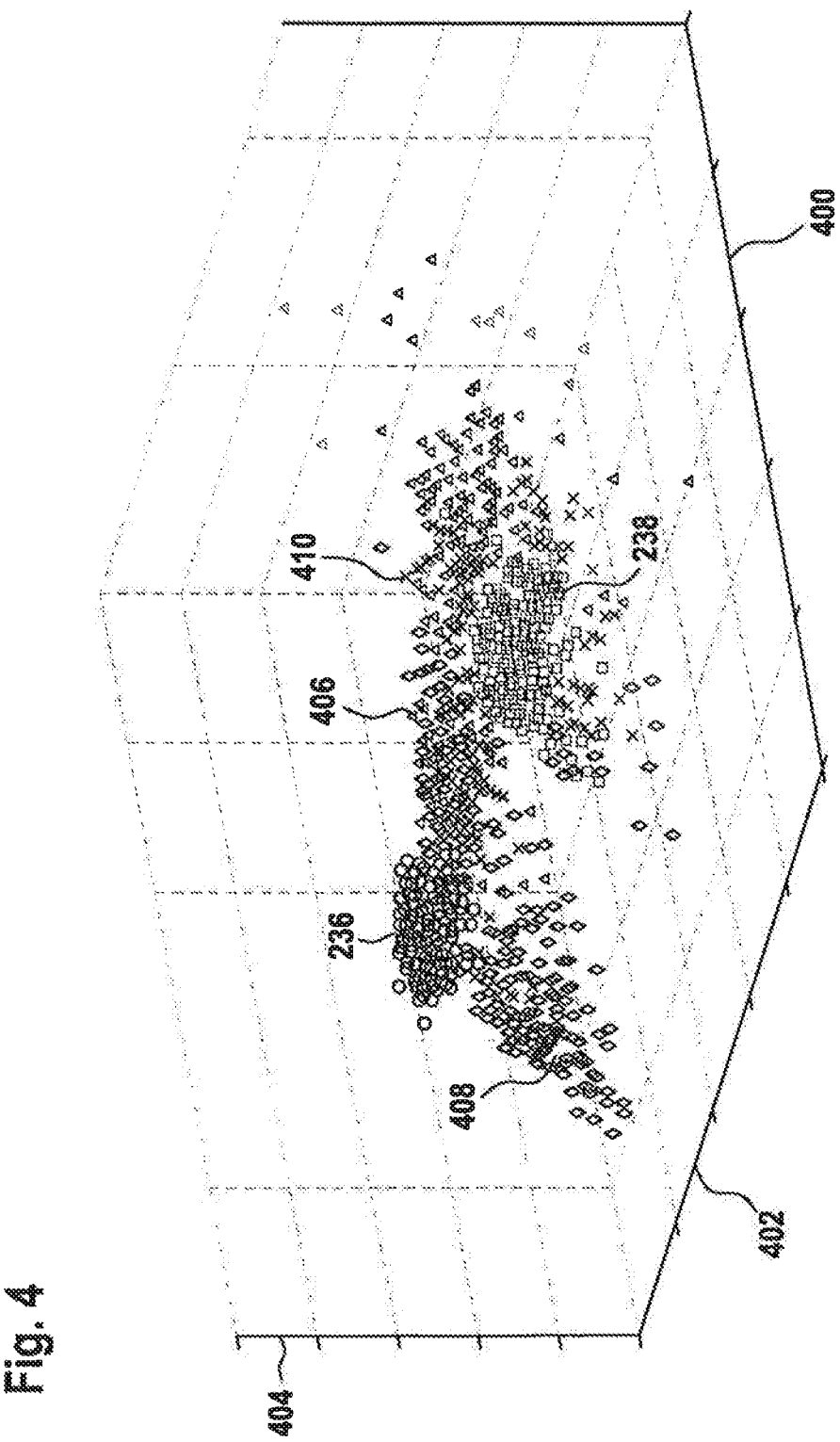
FIGS. 4 to 7 show graphs for representing data clusters of eye opening data, generated according to the method from FIG. 3, according to an exemplary embodiment.

FIG. 4 shows a 3-dimensional Cartesian coordinate system. An eyelid speed of motion in meters per second (m/s) is plotted on abscissa 400. The eye opening degree in meters (m) is plotted on ordinate 402. An eyelid acceleration of motion in meters per second squared (m/s$^2$) is plotted on applicate 404. The coordinate system in FIG. 4 shows a plurality of data records of eye opening data of a vehicle occupant generated and assigned according to the computational method. Many of the eye opening data records are grouped to form data clusters, which are clearly distinguishable from one another by the eye of the observer.

In the representation in FIG. 4, each data cluster represents, in the form of a cloud, one state of the eyes and/or the eyelids of the vehicle occupant considered, the state being different from several categories. Thus, first data cluster 236, which was already explained in connection with FIG. 2 and is formed from a grouping of several data records symbolized by circles, represents a first opening state of the eye or eyes of the vehicle occupant, in which the eye or eyes is/are open.

Second data cluster 238, which was also already explained in connection with FIG. 2 and is formed from a grouping of several data records symbolized by squares, represents a second opening state of the eye or eyes of the vehicle occupant, in which the eye or eyes is/are closed.

A third data cluster 406, which is formed from a grouping of several data records symbolized by triangles, represents a first transition state of the eye or eyes of the vehicle occupant, in which the eye or eyes is/are in an opening phase.

A fourth data cluster 408, which is formed from a grouping of several data records symbolized by rhombuses, represents a second transition state of the eye or eyes of the vehicle occupant, in which the eye or eyes is/are in a closing phase. Data records 410, which represent outliers of the acquired eye opening data, are plotted in the coordinate system in FIG. 4, using crosses.

As the representation in FIG. 4 shows, individual data clusters 236, 238, 406, 408 are characterized by a different individual density and a different individual distribution region in the coordinate system. Thus, data clusters 236 and 238 are delimited in a particularly dense and spatially confined manner. However, data clusters 406 and 408 have a lower density and extend in a larger three-dimensional space, which is delimited less clearly than in the case of data clusters 236 and 238. Since individual data clusters 236, 238, 406, 408 are easy to distinguish from each other and, in particular, outlier values 410 may be identified readily, it is possible to separate and classify the eye states and eye opening states of the vehicle occupant in a robust manner for drowsiness and/or microsleep detection relatively unaffected by measuring error.

Figure 5:
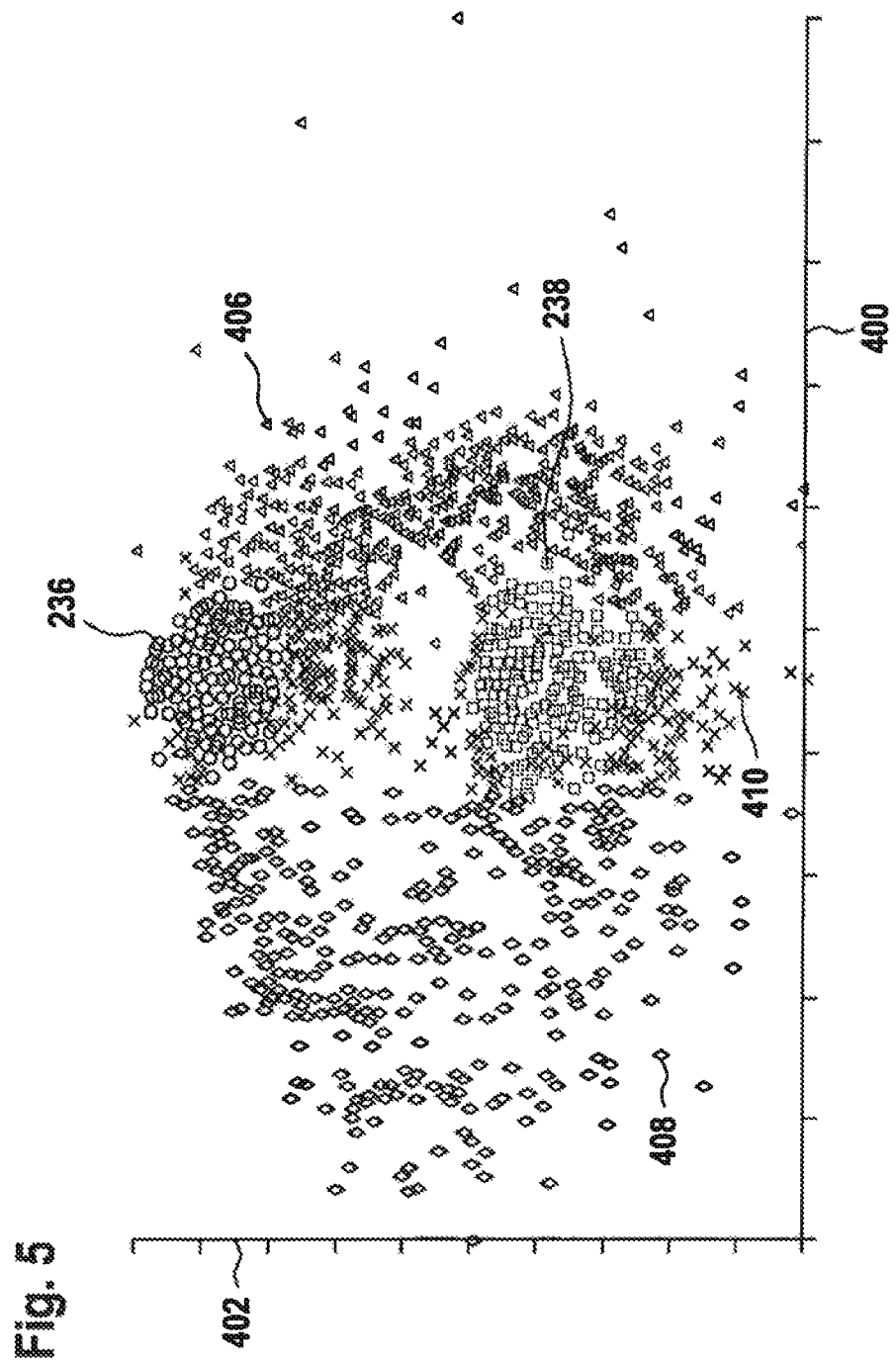

FIG. 5 shows, in a two-dimensional view, the data clusters 236, 238, 406, 408 ascertained in the exemplary computation method, with a view of abscissa 400 and ordinate 402 of the coordinate system from FIG. 4. In this case, the spatial separation of data clusters 236, 238, 406, 408 may easily be seen.

Figure 6:
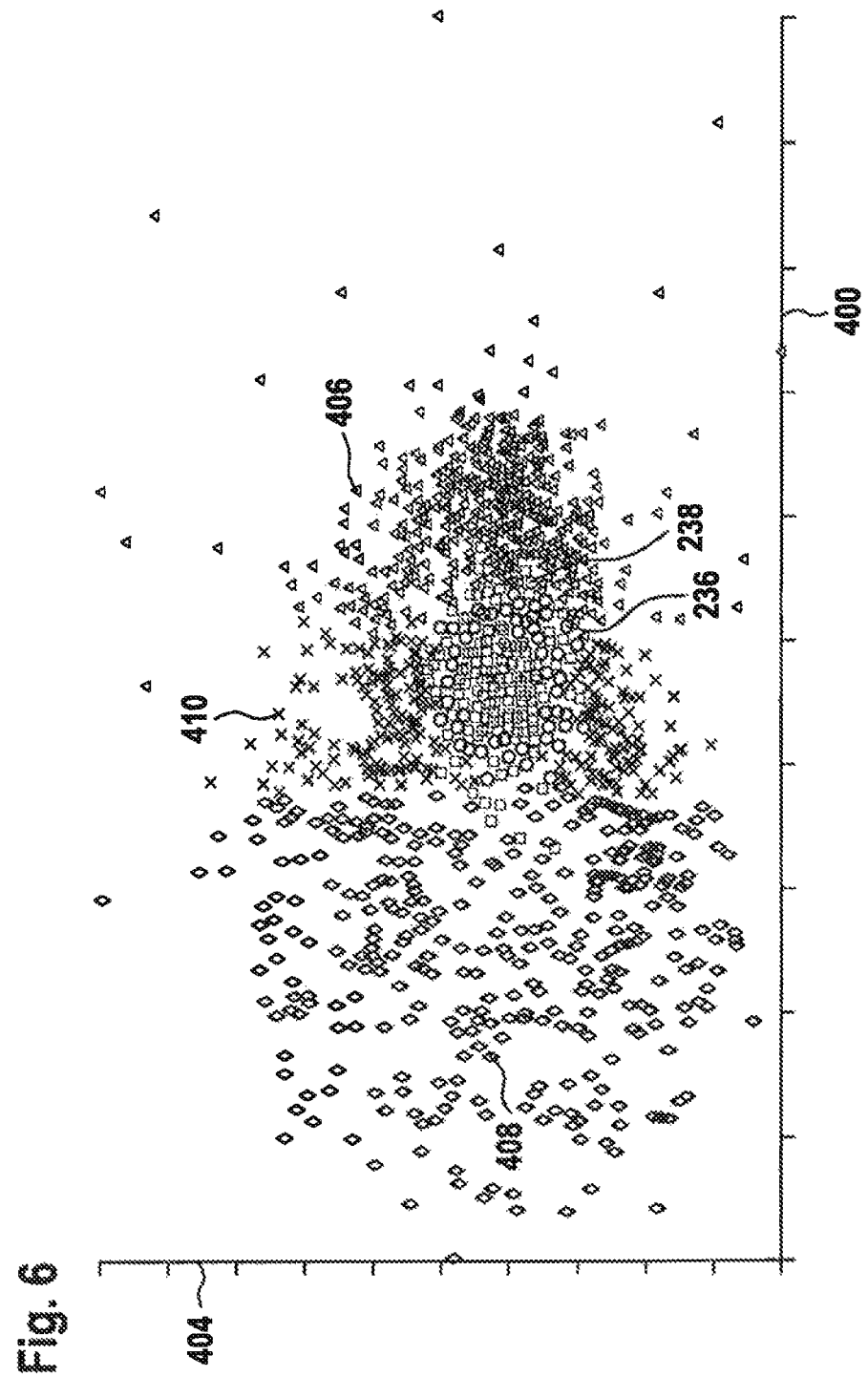

FIG. 6 shows, in a further two-dimensional view, the data clusters 236, 238, 406, 408 ascertained in the exemplary computation method, with a view of abscissa 400 and applicate 404 of the coordinate system from FIG. 4. In this view, the second data cluster 238 representing the closed eyes overlaps the first data cluster 236 of approximately equal size and shape, representing the open eyes. It is also apparent that the fourth data cluster 408 representing the closing eyes is scattered considerably more widely than the third data cluster 406 representing the opening eyes.

Figure 7:
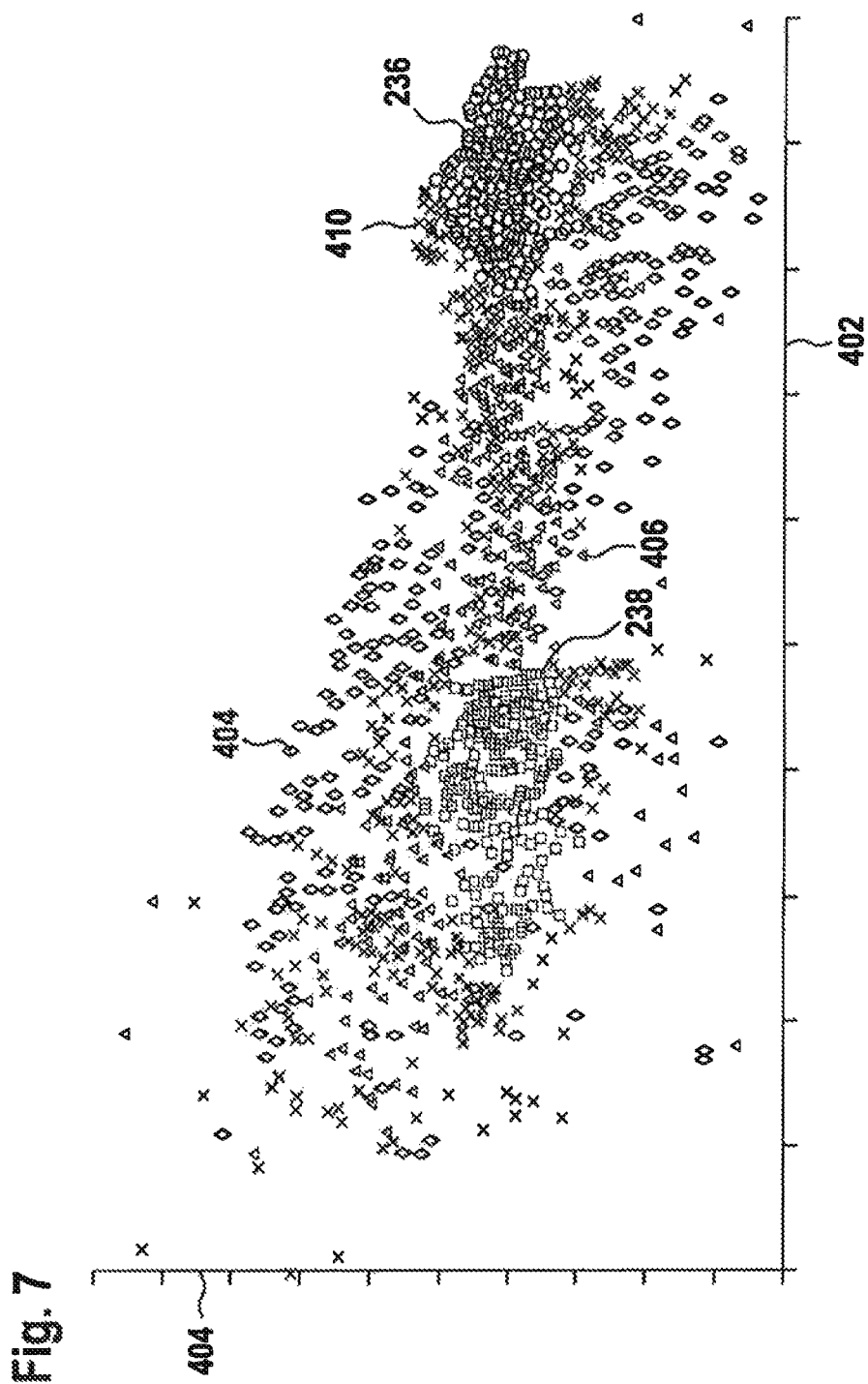

FIG. 7 shows, in a further two-dimensional view, the data clusters 236, 238, 406, 408 ascertained in the exemplary computational method, with a view of ordinate 402 and applicate 404 of the coordinate system from FIG. 4. In this case, as well, the high density of data clusters 236 and 238 is readily apparent.

The new type of computational method described with the aid of FIGS. 4 through 7 and proposed here is summarized once more in the following in an illustrative manner, in light of an exemplary embodiment. Initially, the eye opening data are acquired in a sliding time window having a duration of, e.g., five minutes for each measuring point in the time window. According to one exemplary embodiment, the eye opening data may be processed in an eye closure preprocessing unit or ECP unit explained in further detail in the following FIG. 9.

Eye opening data records formed from the eye opening data and/or their measuring points or acquisition points from the sliding time window described above are subjected to a density-based cluster analysis. In this context, the space, in which the data records are situated, is scanned for regions that have a high density of data records. All of the data records of such a region are assigned to a common cluster 236, 238, 406, or 408. One possible implementation of the density-based cluster analysis is the OPTICS algorithm (cf. Ankerst, Mihael, et al., "OPTICS; ordering points to identify the dustering structure." ACM Sigmod Record. Vol. 28. No. 2. ACM, 1999).

A plurality of these clusters 236, 238, 406 or 408 may be identified, which allows the corresponding data records to be put into different categories. Thus, first data cluster 236 denotes a first category, in which the eyes of the vehicle occupant are open. Second data cluster 238 indicates a second category, in which the eyes of the vehicle occupant are closed. Third data cluster 406 denotes a third category, in which the eyes of the vehicle occupant are in the opening phase. Fourth data cluster 408 indicates a fourth category, in which the eyes of the vehicle occupant are in the closing phase. Outliers 410 in the measurements are graphically represented, as well. Of course, it is possible to represent further clusters, which are based on further measuring and acquisition points. For example, a further cluster may denote glances of the vehicle occupant at the speedometer.

In an above-mentioned further refinement of the concept proposed here, a parameter is determined for each of data clusters 236, 238, 406, 408. In the determination, a center of the respective data cluster 236, 238, 406, 408 may be considered, in order to determine the parameter from an average value of all of the data records within cluster 236, 238, 406, 408. Alternatively, the parameter may be ascertained on the basis of a determination of a center of mass. In this case, the weighted average of all data records within a cluster 236, 238, 406, 408 is taken as a basis. The weighting for each data record is given by the density of the region, in which it is situated.

Since these parameters lie in the same three-dimensional space as the underlying data records, they may be broken down into values for the eye opening degree, the speed of motion and the acceleration of motion of the eyelids of the occupant. Thus, a value for the eye opening degree, which may be used as an eye opening niveau value or EON value for drowsiness and/or microsleep detection, may be deduced from the parameters of clusters 236, 238, 406, 408. This EON value is markedly more stable, that is, subject to fewer fluctuations, than an EON value determined with the aid of conventional methods, since blinking events, glances at the speedometer, etc., do not enter into the computation. Apart from the more robust EON value, a further advantage of the method proposed here is that the data of the different clusters 236, 238, 406, 408 may be used to find blinking events, glances at a speedometer, etc., in the eye opening signal.

Figure 8:
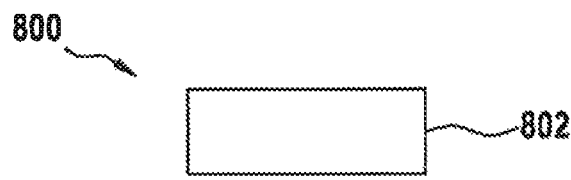
FIG. 8 shows a flow chart of a method for detecting drowsiness and/or microsleep of an occupant of a vehicle, according to an exemplary embodiment.

FIG. 8 shows a flow chart of an exemplary embodiment of a method 800 for detecting drowsiness and/or microsleep of an occupant of a vehicle. In an ascertaining step 802, drowsiness and/or microsleep of the occupant is ascertained, using eye opening data, which has been classified according to the above-described method for classifying eye opening data.

Figure 9:
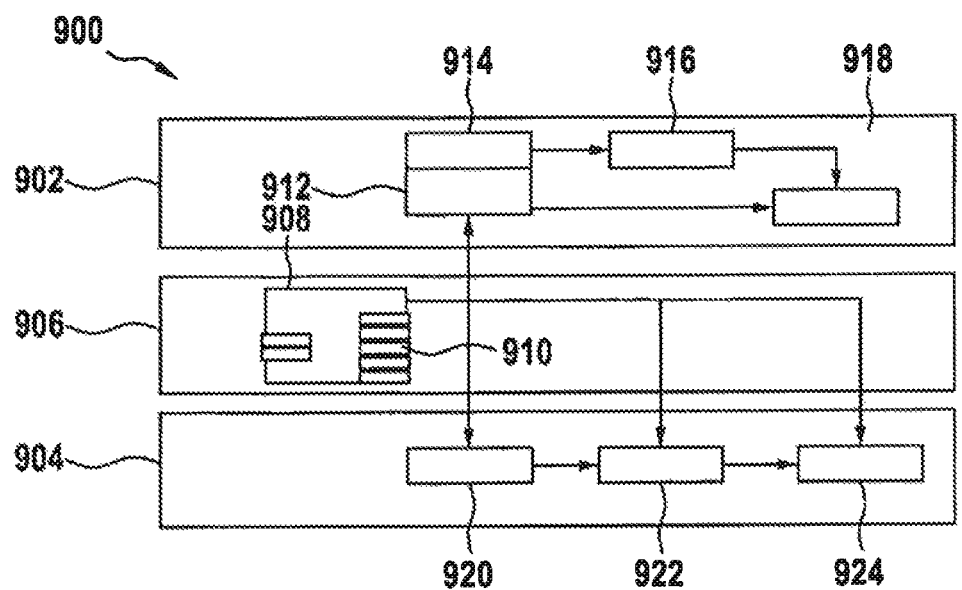
FIG. 9 shows a representation of an architecture of an overall system for monitoring drowsiness and/or microsleep of an occupant of a vehicle, according to an exemplary embodiment.

FIG. 9 shows a representation of an architecture of an overall system 900 for monitoring a driver of a vehicle with regard to drowsiness and/or microsleep, according to an exemplary embodiment.

Overall system 900 includes three main components 902, 904, 906. First main component 902 is referred to as a drowsiness classification unit. Second main component 904 is referred to as a microsleep detection unit. Third main component 906 includes modules 908 used jointly by drowsiness classification unit 902 and microsleep detection unit 904, as well as a device 910 for providing the eye opening niveau or EON. Modules 908 may be referred to as eye closure preprocessing unit or ECP unit 908. Eye closure preprocessing unit 908 includes recording of the closure of the right and left eyes, filtering of the eye closure, measuring of the speed of the eye closure, measuring of the acceleration of the eye closure, the device 910 for providing the EON, and a validation unit.

Eye closure preprocessing unit 908 outputs a current instance of eye closure, a speed of eye closure and the EON.

In drowsiness classification unit 902, these values are used in a blinking event detection unit 912, and blinking events are transmitted to a blinking characteristic computation unit 914.

Blinking characteristic computation unit 914 outputs blinking characteristics to a personal blinking characteristic detection unit 916 and to a module 918 for drowsiness classification. Module 918 inputs a personal blinking behavior from blinking characteristic detection unit 916 and outputs a drowsiness niveau.

In microsleep detection unit 904, the values are used in a personal eye closure detection unit 920, an eye closure detection unit 922 and a module 924 for detecting microsleep.

Personal eye closure detection unit 920 outputs a personal eyes-open niveau and a personal eyes-closed niveau. The two are used by eye closure detection unit 922, in order to provide a binary eyes-open value to module 924. Module 924 outputs microsleep events.

According to one exemplary embodiment, the robust EON ascertained according to the concept put forward here may easily be integrated in overall system 900 for detecting drowsiness and/or microsleep. Alternatively, the computation of the EON may take place within the scope of the eye closure preprocessing in ECP unit 908. The EON is subsequently used within the scope of the blinking event detection and the blinking characteristic computation.

As explained above, the EON indicates how large an average, current separation of the eyelids is in the open state. In the computation of the EON, it is important that possible blinking events, speedometer glances, etc., are not included in the computed value, since it would otherwise be influenced, for instance, by the blinking frequency and period. The higher the frequency and period of the blinking events were to be, the lower the EON resulting from them would turn out.

The presence of the robust EON subject to fewer fluctuations in accordance with the concept put forward here, has several advantages. Thus, simple and robust detection of blinking events, using limiting values that are determined relative to the EON, may be ensured. In addition, simple computation of particular characteristics of the blinking events, such as the blinking amplitude, is possible. Furthermore, this produces the option of computing a PERCLOS value in a robust manner, the value referring to the 90th percentile of the EON as a maximum opening degree.

If an exemplary embodiment includes an "and/or" conjunction between a first feature and a second feature, then this is to be understood to mean that according to one specific embodiment, the exemplary embodiment includes both the first feature and the second feature, and according to a further specific embodiment, the exemplary embodiment includes either only the first feature or only the second feature.

What is claimed is:

1. A method for classifying eye opening data of an eye of an occupant of a vehicle to detect drowsiness and/or microsleep of the occupant, the method comprising:
    generating a first eye opening data record at a first measuring time in a sliding time window, the first eye opening data record including at least one measuring point, which represents a first eye opening degree and/or a first eyelid speed of motion and/or a first eyelid acceleration of motion of the eye of the occupant at the first measuring time;
    acquiring a second eye opening data record at a second measuring time in the sliding time window, the second eye opening data record including at least one acquisition point, which represents a second eye opening degree and/or a second eyelid speed of motion and/or a second eyelid acceleration of motion of the eye of the occupant at the second measuring time;
    executing a cluster analysis, using the at least one measuring point and the at least one acquisition point, to assign at least the first eye opening data record and the second eye opening data record to a first data cluster, to classify the eye opening data, the first data cluster representing an opening state of the eye of the occupant; and
    performing an averaging, using the at least one measuring point and the at least one acquisition point, based on the first eye opening data record and the second eye opening data record being assigned to the first data cluster; to calculate a first parameter of the first data cluster, the first parameter representing a value for an eye opening niveau of the eye of the occupant.

2. The method of claim 1, wherein in the generating, the first eye opening data record includes a further measuring point, which represents a first eye opening degree not represented by the at least one measuring point and/or a first eyelid speed of motion and/or a first eyelid acceleration of motion of the eye of the occupant at the first measuring time; and/or in the acquiring, the second eye opening data record includes a further acquisition point, which represents a second eye opening degree not represented by the at least one acquisition point and/or a second eyelid speed of motion and/or a second eyelid acceleration of motion of the eye of the occupant at the second measuring time; in the execution, the cluster analysis further being executed, using the further measuring point and/or the further acquisition point.

3. The method of claim 1, wherein in the averaging, the at least one measuring point and the at least one acquisition point are averaged in a weighted manner, to determine the first parameter.

4. The method of claim 3, wherein in the averaging, the at least one measuring point is weighted as a function of the at least one acquisition point, in particular, the at least one measuring point being weighted as a function of a value of the at least one acquisition point, to determine the first parameter.

5. The method of claim 1, wherein in the execution, the first eye opening data record is assigned to the first data cluster, and the second eye opening data record is assigned to a second data cluster, to classify the eye opening data; the second data cluster representing a further opening state of the eye of the occupant.

6. The method of claim 5, wherein in the executing, the opening state represents an open eye of the occupant, and the further opening state represents a closed eye of the occupant.

7. The method of claim 1, further comprising:
inputting a third eye opening data record at a third measuring time in the sliding time window, the third eye opening data record including at least one determination point, which represents a third eye opening degree and/or a third eyelid speed of motion and/or a third eyelid acceleration of motion of the eye of the occupant at the third measuring time; in the executing, the cluster analysis being executed, using the at least one determination point of the third eye opening data record, to assign at least the third eye opening data record to a third data cluster, to classify the eye opening data, the third data cluster representing a transition state of the eye of the occupant.

8. The method of claim 7, wherein the transition state represents an opening phase of the eye of the occupant or a closing phase of the eye of the occupant.

9. A method for detecting drowsiness and/or microsleep of an occupant of a vehicle, the method comprising:
ascertaining drowsiness and/or microsleep, using eye opening data; wherein the eye opening data is classified by classifying the eye opening data of an eye of the occupant of the vehicle to detect the drowsiness and/or the microsleep of the occupant, by performing the following:
generating a first eye opening data record at a first measuring time in a sliding time window, the first eye opening data record including at least one measuring point, which represents a first eye opening degree and/or a first eyelid speed of motion and/or a first eyelid acceleration of motion of the eye of the occupant at the first measuring time;
acquiring a second eye opening data record at a second measuring time in the sliding time window, the second eye opening data record including at least one acquisition point, which represents a second eye opening degree and/or a second eyelid speed of motion and/or a second eyelid acceleration of motion of the eye of the occupant at the second measuring time;
executing a cluster analysis, using the at least one measuring point and the at least one acquisition point, to assign at least the first eye opening data record and the second eye opening data record to a first data cluster, to classify the eye opening data, the first data cluster representing an opening state of the eye of the occupant; and
performing an averaging, using the at least one measuring point and the at least one acquisition point, based on the first eye opening data record and the second eye opening data record being, assigned to the first data cluster, to calculate a first parameter of the first data cluster, the first parameter representing a value for an eye opening niveau of the eye of the occupant.

10. A device, comprising:
a processing device configured to classify eye opening data of an eye of an occupant of a vehicle to detect drowsiness and/or microsleep of the occupant, by performing the following:
generating a first eye opening data record at a first measuring time in a sliding time window, the first eye opening data record including at least one measuring point, which represents a first eye opening degree and/or a first eyelid speed of motion and/or a first eyelid acceleration of motion of the eye of the occupant at the first measuring time;
acquiring a second eye opening data record at a second measuring time in the sliding time window, the second eye opening data record including at least one acquisition point, which represents a second eye opening degree and/or a second eyelid speed of motion and/or a second eyelid acceleration of motion of the eye of the occupant at the second measuring time;
executing a cluster analysis, using the at least one measuring point and the at least one acquisition point, to assign at least the first eye opening data record and the second eye opening data record to a first data cluster, to classify the eye opening data, the first data duster representing an opening state of the eye of the occupant; and
performing an averaging, using the at least one measuring point and the at least one acquisition point, based on the first eye opening data record and the second eye opening data record being assigned to the first data duster, to calculate a first parameter of the first data duster, the first parameter representing a value for an eye opening niveau of the eye of the occupant.

11. A non-transitory computer readable medium having a computer program, which is executable by a processor, comprising:
a program code arrangement having program code for classifying eye opening data of at an eye of an occupant of a vehicle to detect drowsiness and/or microsleep of the occupant, by performing the following:
generating a first eye opening data record at a first measuring time in a sliding time window, the first eye opening data record including at least one measuring point, which represents a first eye opening degree and/or a first eyelid speed of motion and/or a first eyelid acceleration of motion of the eye of the occupant at the first measuring time;
acquiring a second eye opening data record at a second measuring time in the sliding time window, the second eye opening data record including at least one acquisition point, which represents a second eye opening degree and/or a second eyelid speed of motion and/or a second eyelid acceleration of motion of the eye of the occupant at the second measuring time; and
executing a cluster analysis, using the at least one measuring point and the at least one acquisition point, to assign at least the first eye opening data record and the second eye opening data record to a first data cluster, to classify the eye opening data, the first data cluster representing an opening state of the eye of the occupant; and
performing an averaging, using the at least one measuring point and the at least one acquisition point, based on the first eye opening data record and the second eye opening data record being assigned to the first data cluster, to calculate a first parameter of the first data cluster, the first parameter representing a value for an eye opening niveau of the eye of the occupant.

12. The computer readable medium of claim 11, wherein in the generating, the first eye opening data record includes a further measuring point, which represents a first eye opening degree not represented by the at least one measuring point and/or a first eyelid speed of motion and/or a first eyelid acceleration of motion of the eye of the occupant at the first measuring time; and/or in the acquiring, the second eye opening data record includes a further acquisition point, which represents a second eye opening degree not represented by the at least one acquisition point and/or a second eyelid speed of motion and/or a second eyelid acceleration of motion of the eye of the occupant at the second measuring time; in the execution, the cluster analysis further being executed, using the further measuring point and/or the further acquisition point.

* * * * *